United States Patent
Hibner et al.

(10) Patent No.: US 6,432,064 B1
(45) Date of Patent: Aug. 13, 2002

(54) BIOPSY INSTRUMENT WITH TISSUE MARKING ELEMENT

(75) Inventors: John A. Hibner, Mason; James R. Giordano, Milford; Scott D. Wampler, Westchester, all of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/829,085

(22) Filed: Apr. 9, 2001

(51) Int. Cl.[7] ............................................... A61B 10/00
(52) U.S. Cl. ........................ 600/564; 600/566; 128/897
(58) Field of Search .................. 600/564, 424, 600/565, 431, 566, 567; 606/167, 116, 170, 130; 604/22, 164.01, 164.11; 128/897, 898

(56) References Cited

U.S. PATENT DOCUMENTS

| | | |
|---|---|---|
| 4,995,877 A | 2/1991 | Ams et al. |
| 5,217,478 A | 6/1993 | Rexroth |
| 5,295,990 A | 3/1994 | Levin |
| 5,526,822 A | 6/1996 | Burbank et al. |
| 5,543,695 A | 8/1996 | Culp et al. |
| 5,578,030 A | 11/1996 | Levin |
| 5,602,449 A | 2/1997 | Krause et al. |
| 5,643,304 A | 7/1997 | Schechter et al. |
| 5,685,838 A | 11/1997 | Peters et al. |
| 5,692,519 A * | 12/1997 | Luderer et al. ............. 600/567 |
| 5,769,086 A | 6/1998 | Ritchart et al. |
| 5,775,333 A | 7/1998 | Burbank et al. |
| 5,788,651 A | 8/1998 | Weilandt |
| 5,830,219 A | 11/1998 | Bird et al. |
| 5,849,023 A | 12/1998 | Mericle |
| 5,891,157 A | 4/1999 | Day et al. |
| 5,902,310 A * | 5/1999 | Foerster et al. ............. 606/142 |
| 5,951,575 A | 9/1999 | Bolduc et al. |
| 5,980,469 A | 11/1999 | Burbank et al. |
| 6,007,497 A | 12/1999 | Huitema |
| 6,019,733 A | 2/2000 | Farascioni |
| 6,036,698 A | 3/2000 | Fawzi et al. |
| 6,077,230 A * | 6/2000 | Gregoire et al. ............. 600/566 |
| 6,080,113 A | 6/2000 | Heneveld et al. |
| 6,086,544 A | 7/2000 | Hibner et al. |
| 6,093,154 A | 7/2000 | Burek et al. |
| 6,120,462 A | 9/2000 | Hibner et al. |
| 6,228,055 B1 * | 5/2001 | Foerster et al. ............. 604/116 |
| 6,234,177 B1 * | 5/2001 | Barsch ........................ 128/897 |
| 6,261,243 B1 * | 7/2001 | Burney et al. .............. 600/564 |

FOREIGN PATENT DOCUMENTS

| | | |
|---|---|---|
| WO | WO95/08959 A1 | 4/1995 |
| WO | WO96/33652 A1 | 10/1996 |
| WO | WO98/25556 A1 | 6/1998 |
| WO | WO98/38919 A3 | 9/1998 |
| WO | WO99/15079 A1 | 4/1999 |
| WO | WO99/44505 A1 | 9/1999 |
| WO | WO00/12010 A1 | 3/2000 |
| WO | WO00/18304 A2 | 4/2000 |
| WO | WO00/38577 A2 | 7/2000 |

OTHER PUBLICATIONS

The Best Choice in Vacuum Assisted Breast Biopsy (MIB); Copy 1998 A Division of United States Surgical Corporation, Printed in USA. 558452 pp. 7.5M 6.98.

* cited by examiner

Primary Examiner—Kevin Shaver
Assistant Examiner—Charles Marmor, II

(57) ABSTRACT

A biopsy probe for the collection of at least one soft tissue sample from a surgical-patient. The biopsy probe has a handle, having a distal end and a proximal end, for holding the probe. The probe further includes an elongated needle, located at the distal end of the handle. The needle has a sharpened distal end for piercing tissue and a bowl for receiving a tissue mass. The probe has a cutter for severing the tissue mass received in the bowl, and at least one tissue marker element to apply a mark to the exterior of the tissue so the radial orientation of the tissue can later be determined.

22 Claims, 8 Drawing Sheets

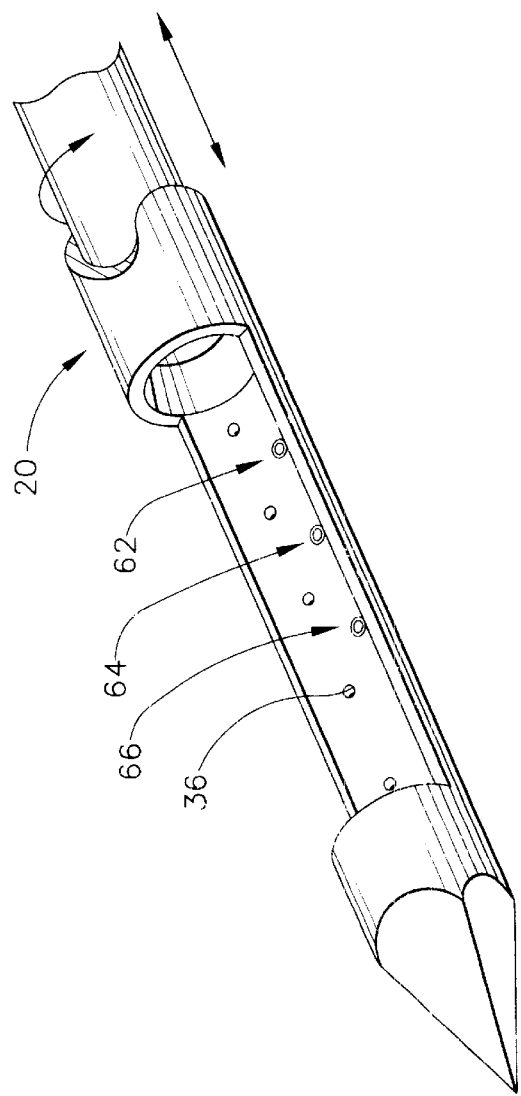
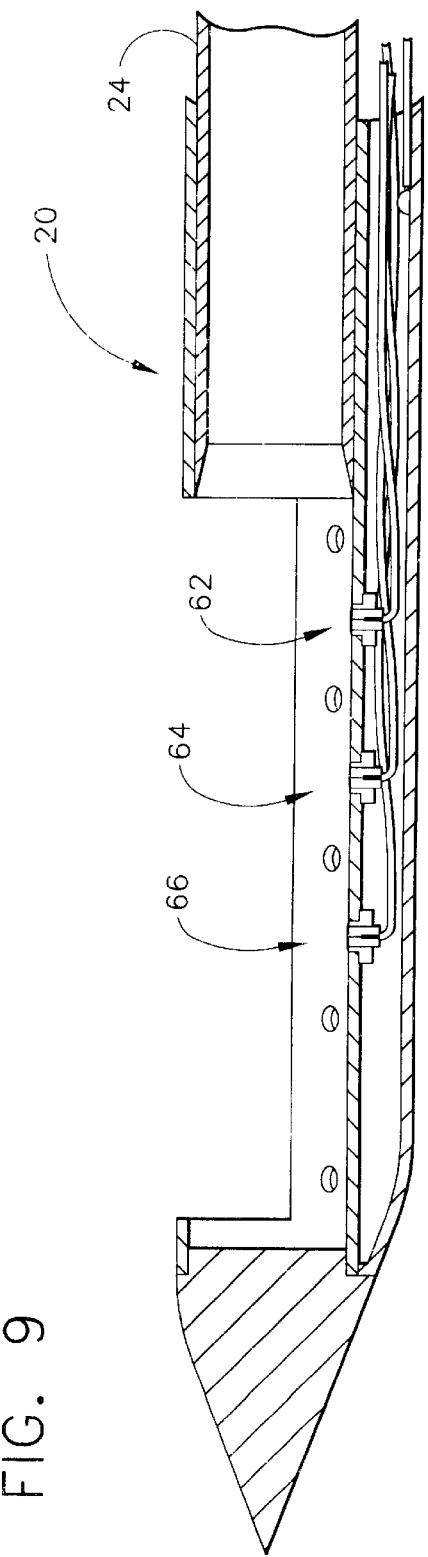
FIG. 9
FIG. 10

BIOPSY INSTRUMENT WITH TISSUE MARKING ELEMENT

FIELD OF THE INVENTION

The present invention relates, in general, to biopsy instruments and methods of taking biopsies and, more particularly, to a percutaneous biopsy instrument containing an element adapted to mark a biopsy specimen prior to harvesting.

BACKGROUND OF THE INVENTION

The diagnosis and treatment of patients with cancerous tumors, pre-malignant conditions, and other disorders has long been an area of intense investigation. Noninvasive methods for examining tissue are palpation, X-ray, MRI, CT, and ultrasound imaging. When the physician suspects that a tissue may contain cancerous cells, a biopsy may be done either in an open procedure or in a percutaneous procedure.

For an open procedure, a scalpel is used by the surgeon to create a large incision in the tissue in order to provide direct viewing and access to the tissue mass of interest. Removal of the entire mass (excisional biopsy) or a part of the mass (incisional biopsy) is done. The excised mass of tissue is examined by the surgeon and then by a pathologist using more precise means to determine if all of the cancerous tissue has been excised. Through direct visualization and palpation the surgeon inspects the excised tissue mass to determine if cancer may exist at the edges of the excised mass. This is followed by the pathologist examining the mass using various techniques to determine if cancer cells are near the edge. To aid the pathologist the surgeon typically identifies the in situ orientation of the mass. This is done by inserting sutures at predetermined locations around the edges of the mass or by marking the edges of the mass with a stain, commonly India ink. If the pathologist then determines that there are cancer cells near one of the edges of the mass the pathologist can direct the surgeon to remove additional tissue from the patient in the area corresponding to the locators marked on the original tissue specimen.

For a percutaneous biopsy, a needle-like instrument is used. An example of a percutaneous biopsy device is the Mammotome™ biopsy system available from Ethicon Endo-Surgery, Inc., Cincinnati, Ohio. Mammotome works through a very small incision to access the tissue mass of interest and to obtain a tissue sample for examination and analysis. Multiple tissue specimens can be removed through a single insertion. The Mammotome biopsy probe typically is rotated about its longitudinal axis at predetermined increments to a new position as each specimen is harvested. Using this technique multiple adjacent tissue samples can be removed. Multiple 360 degree revolutions of the probe may be necessary to remove all of the desired tissue.

The advantages of the percutaneous method as compared to the open method are significant: less recovery time for the patient, less pain, less surgical time, lower cost, less risk of injury to adjacent bodily tissues such as nerves, and less disfigurement of the patient's anatomy. However, since the tissue mass is removed in multiple pieces, reconstruction of the mass from the harvested pieces is challenging. With great care the clinician can identify and document the order of each specimen's removal. And, because each tissue specimen is cylindrical in geometry and the distal to proximal end orientation is maintained during the specimen harvesting procedure, the clinician can maintain the distal to proximal end orientation of the specimens during post biopsy analysis. What the clinician does not know, however, is the radial orientation of the cylindrical biopsy specimen as it was prior to being harvested. Once the specimen is severed and captured by Mammotome's rotating cutter, in situ radial orientation is lost. Lack of this information makes it difficult to accurately reconstruct the tissue mass to determine if all cancerous cells have been harvested. Without radial orientation information, especially on the last biopsy specimens to be taken since they typically represent the outer perimeter of the entire tissue mass harvested, it's difficult for the pathologist to direct the clinician back to a specific area at the biopsy site if additional tissue is needed.

Radial orientation of other biopsy devices has also been a problem. In the prior art, PCT application number WO0012010 to Sirimanne et al describes a percutaneous tissue biopsy device incorporating a rotating wire which produces a helical cut. A tissue mass can be removed through a comparatively small opening and readily reconstructed. Unfortunately, however, the in situ orientation of the tissue mass is lost once removed from the patient. U.S. Pat. No. 6,036,698 to Fawzi et al describes a percutaneous tissue biopsy device using an expandable ring cutter. A relatively large tissue specimen can be removed through a comparatively small device. Again no means is described in this invention for marking the in situ orientation of the tissue specimen and, therefor, orientation is lost upon removal from the patient. U.S. Pat. No. 5,578,030 to Levin describes a biopsy needle with a cauterization feature. In this invention tissue specimens are harvested through a stylet contained within a biopsy needle. Once the specimen is taken, the biopsy needle is energized to cauterize the wound caused by the taking of the tissue specimen. This invention features a means for insulating the excised tissue specimen from the cauterizing heat. No means is described for marking in situ orientation of the specimen. Similarly, U.S. Pat. No. 5,295,990 to Levin describes a tissue biopsy device with pivoting cutting jaws. Once the tissue specimen is severed, by closing the cutting jaws, the jaws are energized with electric current to cauterize tissue surrounding the jaws. An insulating material covers the inside of the jaws where the tissue specimen resides to protect the specimen from the cauterization heat. Again, no means are described to mark the specimen to identify orientation.

What is needed is a percutaneous biopsy instrument incorporating an element for marking the orientation of each specimen in situ, prior to harvesting and examination.

SUMMARY OF THE INVENTION

A biopsy probe for the collection of at least one soft tissue sample from a surgical patient. The biopsy probe has a handle, having a distal end and a proximal end, for holding the probe. The probe further includes an elongated needle, located at the distal end of the handle. The needle has a sharpened distal end for piercing tissue and a bowl for receiving a tissue mass. The probe has a cutter for severing the tissue mass received in the bowl, and at least one tissue marker element to apply a mark to the exterior of the tissue so the radial orientation of the tissue can later be determined.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 9 is an isometric view of the distal end of the biopsy probe of FIG. 2, illustrating multiple marker elements;

FIG. 10 is a longitudinal section view of the distal end of the biopsy probe of FIG. 9;

DETAILED DESCRIPTION OF THE INVENTION

Figure 1:
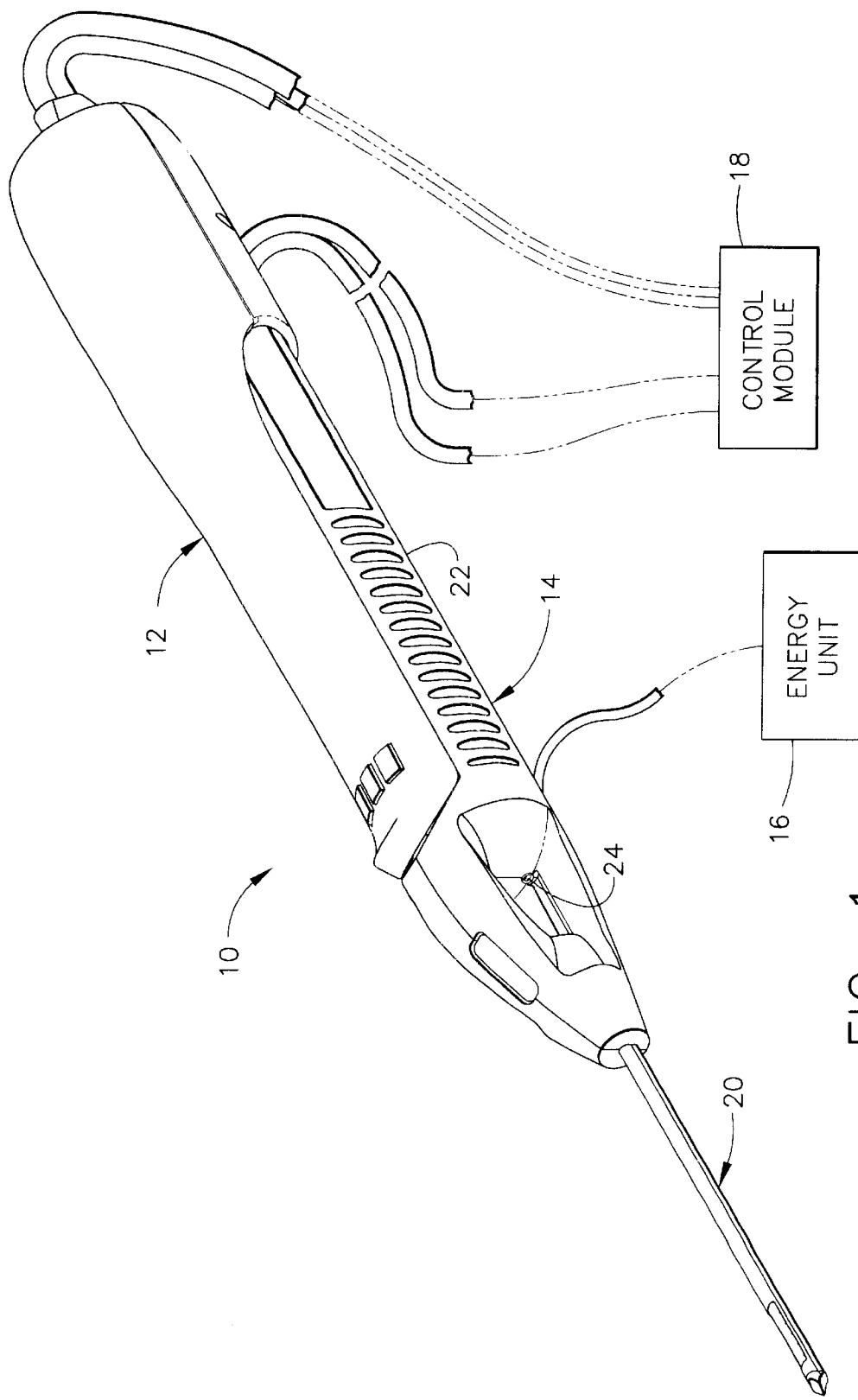
FIG. 1 is an isometric view of a biopsy apparatus, showing the biopsy probe of FIG. 2 assembled to a handle, and schematic representations of a control module and energy unit.
Figure 2:
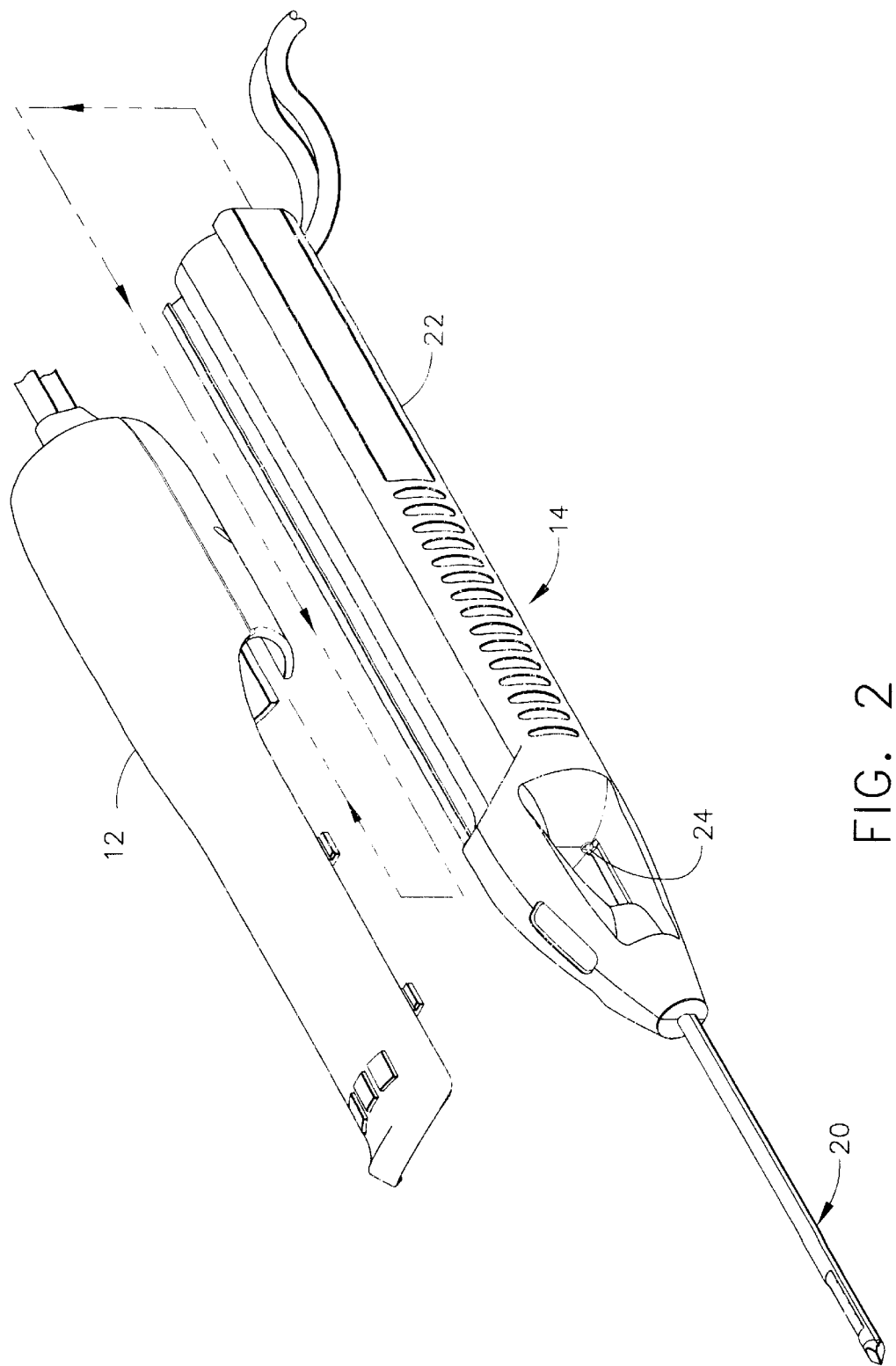
FIG. 2 is an isometric view of the biopsy probe of the present invention and handle shown separated.

Referring to FIG. 1 and FIG. 2 wherein like numerals indicate the same element throughout the views, there is shown a biopsy apparatus 10 made in accordance with the present invention. Many of the features of apparatus 10 are known to those skilled in the art, and indeed many of the known features are described in U.S. Pat. No. 6,086,544 issued to Hibner et al which is hereby incorporated herein by reference. Biopsy apparatus 10 is comprised of a handle 12, which operably connects to probe 14. A suitable handle 12 is commercially available as part no. HHHC1, and a suitable probe 14 is commercially available as part no. MHH11, from Ethicon Endo-Surgery, Inc., Cincinnati, Ohio. Needle 20 is located at the distal end of probe 14. At the proximal end of probe 14 is probe driver 22. Contained within the housing of probe driver 22 are gears (not shown) which effect rotation and translation of cutter 24. Control module 18 is operatively connected to handle 12 and contains motors that control rotation and translation of cutter 24 located in probe 14. Control module 18 also contains a vacuum pump and reservoir that is fluidly connected to probe 14. A suitable control module is available commercially as part no. SCM12, from Ethicon Endo-Surgery, Inc., Cincinnati, Ohio. and is described in U.S. Pat. No. 6,120,462 to Hibner et al, which is hereby incorporated herein by reference. Energy unit 16 is operably connected to probe 14 and is used to energize marker element 26 (see FIG. 3), which will be described in detail later.

Figure 3:
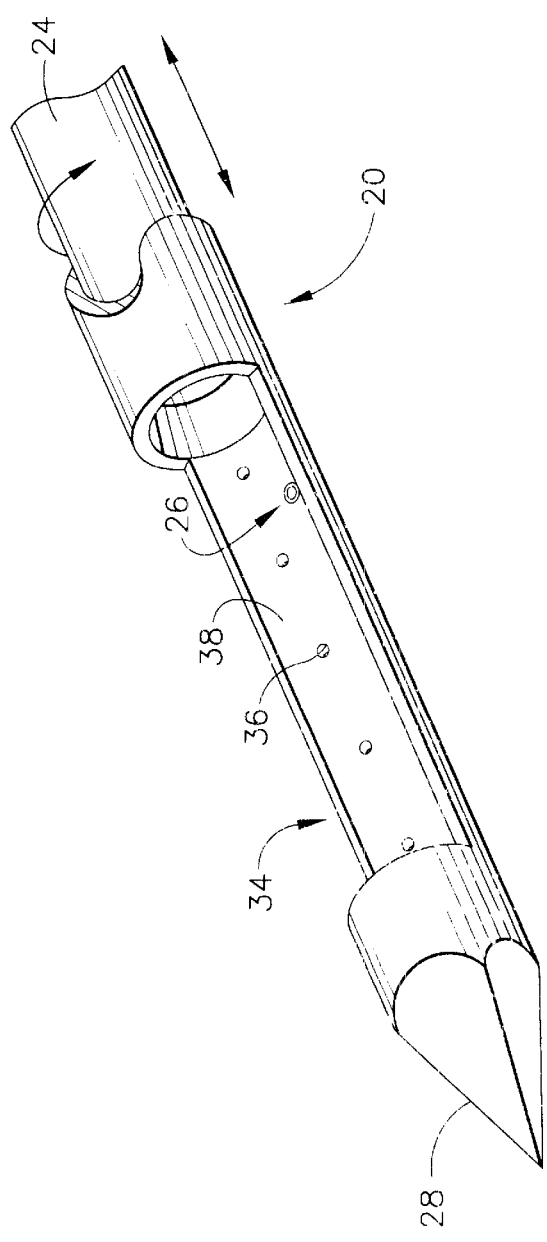
FIG. 3 is an isometric view of the distal end of the biopsy probe of FIG. 2, illustrating the marker element of the present invention.
Figure 4:
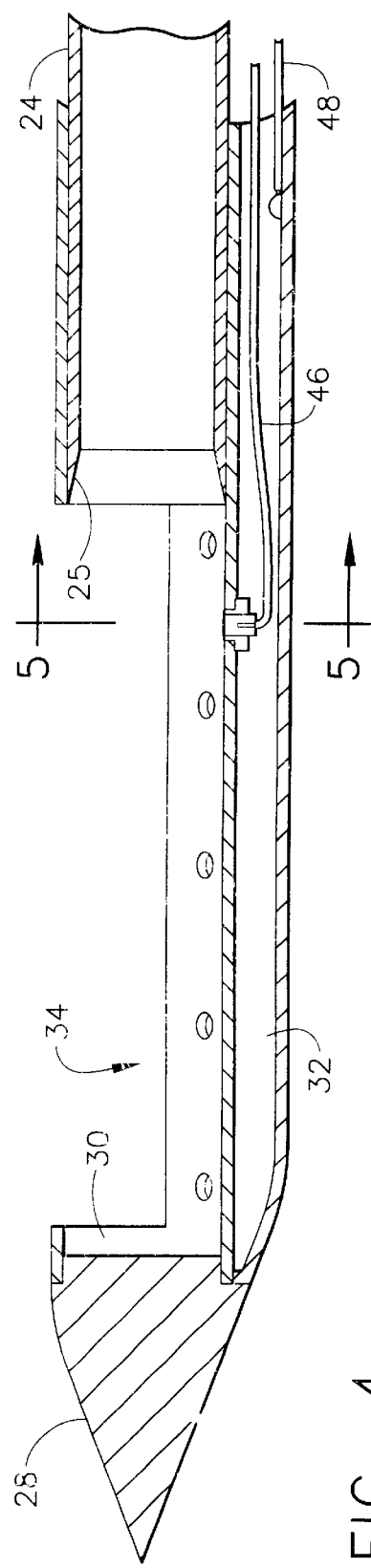
FIG. 4 is a longitudinal section view of the distal end of the biopsy probe illustrated in FIG. 3.
Figure 5:
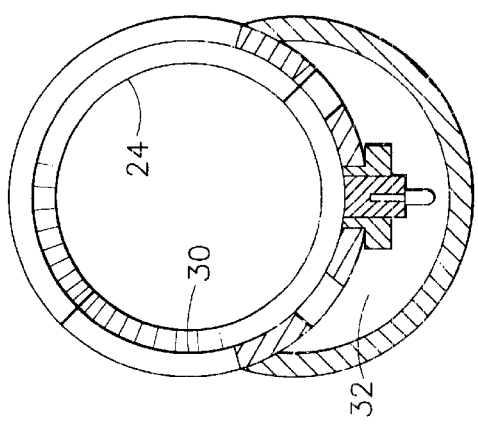
FIG. 5 is a cross sectional view taken along line 5—5 of FIG. 4.

FIG. 3, FIG. 4 and FIG. 5 illustrate the distal end of needle 20. In the preferred embodiment needle 20 is made of electrically conductive materials such as, for example, stainless steel. Needle 20 is comprised of an upper lumen 30 and a lower lumen 32. Vacuum holes 36 are located in the bottom of bowl 34 and allow for fluid communication between bowl 34, located in upper lumen 30, and lower lumen 32. In the preferred embodiment two parallel rows of vacuum holes are located in bowl bottom 38, straddling the center axis of upper lumen 30. Cutter 24 is a tubular structure with a sharpened distal end 25 and can rotate and translate within upper lumen 30. At the most distal end of needle 20 is fixedly attached piercing element 28.

To better understand the present invention, a brief description of the process of taking a biopsy sample from the breast follows. The process, including the novel elements of the present invention, is described in greater detail later:

Images of the breast are taken, typically using x-ray or ultrasound, to locate the suspect lesion in the breast. Needle 20 is advanced into the lesion with bowl 34 placed at the location where the desired tissue specimen is to be harvested. Vacuum is applied to bowl 34 causing the prolapse of tissue against bowl bottom 38 and against marker element 26. At this point marker element 26, the focus of the present invention, is momentarily energized leaving a distinct mark on the surface of the tissue where it contacts. Cutter 24 rotates and is advanced distally through bowl 34 severing the tissue. Vacuum is terminated at bowl 34 and cutter 24 is retracted proximal carrying with it the severed tissue specimen. The specimen is retrieved at the proximal end of needle 20 by the clinician. The clinician may now rotate needle 20 about its axis and repeat the process to take additional samples if desired.

Referring again to FIGS. 3 through 5, within bowl bottom 38 at the base of bowl 34 is located marker element 26. In the illustrated embodiment marker element 26 is located at the proximal end of bowl 34 between parallel rows of vacuum holes 36. However, it could be located anywhere along the bowl bottom 38.

Figure 6:
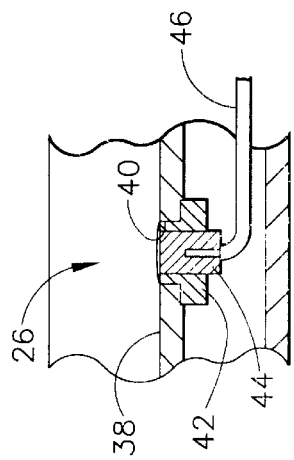
FIG. 6 is an enlarged fragmentary cross sectional view taken from FIG. 4 showing details of the marker element of the present invention.

FIG. 6 illustrates in detail the preferred embodiment of marker element 26. Marker hole 40 is located in bowl bottom 38. Marker element 26 comprises insulator ring 42, which is generally cylindrical with a hole through its center. Insulator ring 42 is made from any commonly available electrical insulating material such as, for example, ceramic and is fixedly attached within marker hole 40 by adhesive or mechanical means. Marker rod 44 is generally cylindrical and made of an electrically conductive material such as, for example, steel and is fixedly attached within the hole in insulator ring 42 by adhesive or mechanical means. First connector wire 46, which is a commonly available electrically conductive wire with insulation, is connected at one end to marker rod 44 and at the other end to energy unit 16 (see FIG. 1). Entire marker element 26 is mounted flush with bowl bottom 38 so that it will not interfere with the travel of cutter 24 through bowl 34. Second conductor wire 48, an electrically conductive wire with insulation, is connected at one end to needle 20 (see FIG. 4) and at the other end to energy unit 16 (see FIG. 1).

In the preferred embodiment of this invention energy unit 16 is an RF generator, commonly known and available in the medical arts. Marker rod 44 is connected to energy unit 16 via first conductor wire 46 and acts as the positive or charged conductor while needle 20 is connected to energy unit 16 via second conductor wire 48 as a ground. This arrangement would be commonly known as bipolar. Hence, applying RF energy to marker element 26 will cauterize in a localized area at marker rod 44 any tissue in contact with marker rod 44 and needle 20, leaving a visible, distinct mark.

It would be evident to one skilled in the art that the arrangement just described could alternately be configured as monopolar by removing second conductor wire 48 from needle 20 and instead attaching second conductor wire 48 between energy unit 16 and the body of the patient. The patient's body is now a ground. Because needle 20 is no longer required to be electrically conductive, needle 20 can be fabricated from a non-electrically conductive material such as, for example, thermoplastic. This is very important when the biopsy instrument is used in some imaging environments such as MRI.

Figure 7:
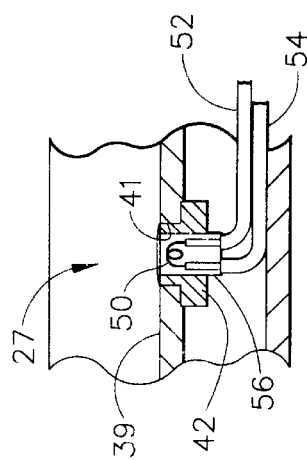
FIG. 7 is an enlarged fragmentary cross sectional view similar to FIG. 6, illustrating a second, alternate embodiment of the marker element.

FIG. 7 illustrates a second, alternate embodiment of the present invention. Second alternate marker element 27 comprises insulator ring 42, fixedly attached within second marker hole 41 in second bowl bottom 39. Heater housing 56, generally cylindrical in shape with a counter bore along its center axis, is made of a thermally conductive material and is fixedly attached within the hole in insulator ring 42. Heater 50 is made of an electrically resistive wire material such as, for example, tungsten and is fixedly attached within heater housing 56 using commonly available potting materials such as, for example, epoxy. Third conductor wire 52 and fourth conductor wire 54 are electrically conductive insulated wires and electrically connect the ends of heater 50 to an energy unit, similar to that of energy unit 16. In this alternate embodiment the energy unit is an electric current source capable of supplying controlled electric current to heater 50 in second marker element 27. Hence, tissue coming into contact with heater housing 56, which is made hot when current is supplied to heater 50, will be cauterized, leaving a visible, distinct mark in the localized area of heater housing 50. It should be evident that in this embodiment needle 20 may be constructed of an electrically conductive or non-electrically conductive material.

Figure 8:
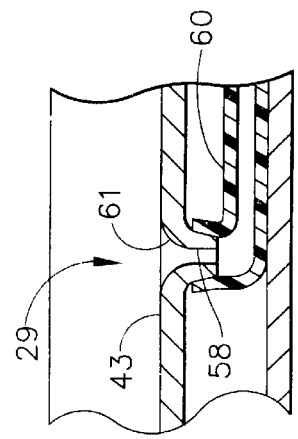
FIG. 8 is an enlarged fragmentary cross sectional view similar to FIG.6, illustrating a third, alternate embodiment of the marker element.

FIG. 8 illustrates a third, alternate embodiment of the present invention. Third alternate marker element 29 comprises hole 61 pierced through third bowl bottom 43 and the perimeter surface of hole 61 is extruded to create flange 58. Tube 60 is fixedly attached to flange 58 using commonly available adhesives. Tube 60 may be made of a flexible material such as, for example, vinyl. The other end of tube 60 is attached to a unit which preferably is a fluid reservoir such as, for example, a syringe. Tissue staining fluid such as a dye, for example, India ink, commonly used in the medical arts, may be placed in the fluid reservoir. Tube 60 fluidly connects the fluid reservoir to hole 61 in third bowl bottom 43. Hence, staining fluid may be injected by a syringe through tube 60 and through hole 61 leaving a visible, distinct mark on tissue in contact with hole 61.

Referring now to FIG. 9 and FIG. 10, multiple marker elements may be incorporated into needle 20. Up to this point the use of only a single marker element 26 to make a single mark on the tissue specimen, as a guide to in situ orientation, has been discussed. FIGS. 9 & 10 illustrate first, second, and third marker elements 62, 64, and 66 respectively. The marker elements may be constructed as described previously. Each marker element may be connected individually to energy unit 16, allowing first marker element 62, second marker element 64, and third marker element 66 to be controlled individually. Energizing various combinations of marker elements to mark each specimen could give the clinician more information on each tissue specimen, based on the number and spacing of the marks. For example, different combinations of marker elements being activated to mark each specimen would provide information to the clinician not only identifying orientation of each specimen, but could also provide sequence numbering on the specimen. For example, the first tissue specimen may be identified by one mark, caused by the activation of only the most proximal first marker element 62. The second specimen may be identified by two marks, created by activating first marker element 62 and adjacent second marker element 64. The third specimen may be identified by activating first, second, and third marker elements 62, 64, and 66 respectively. The fourth specimen may be identified by activating first marker element 62 and third marker element 66, the clinician being required to note the spacing between the marks so as not to confuse specimen four with specimen two. The more marker elements available, the more mark combinations, the more specimens that can be identified. Ideally, mark combinations would be computer controlled at energy unit 16.

Figure 11:
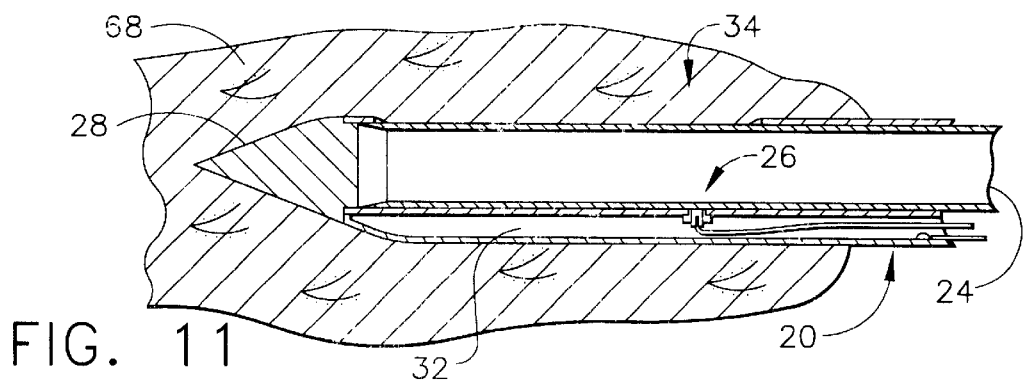
FIG. 11 is a longitudinal section view of the biopsy probe of the present invention, similarly illustrated in FIG. 4, showing the cutter in its most distal position and showing the biopsy probe inserted into the targeted tissue mass.
Figure 12:
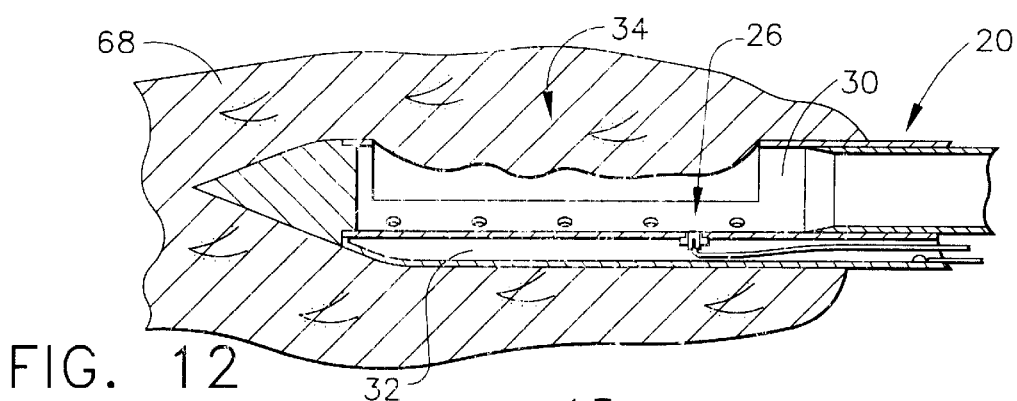
FIG. 12 is a longitudinal section view of the biopsy probe similar to FIG. 11, illustrating the retraction of the cutter in preparation for taking a tissue sample.
Figure 13:
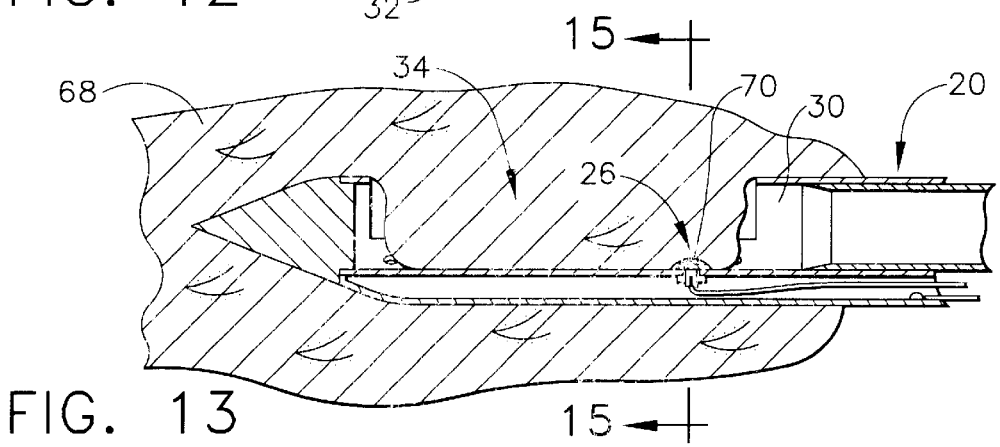
FIG. 13 is a longitudinal section view of the biopsy probe similar to FIG. 11, illustrating the prolapse of tissue into the tissue bowl following the application of vacuum and illustrating the tissue making contact with the marker element and the marker element being energized to mark the tissue specimen.
Figure 14:
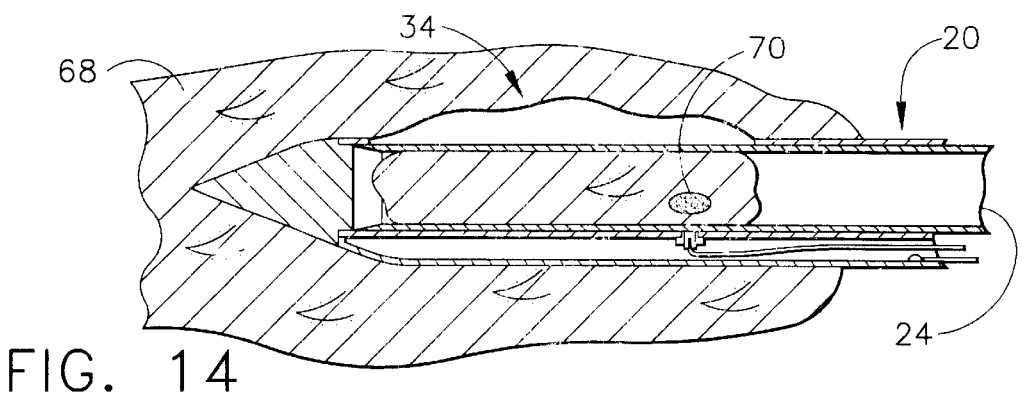
FIG. 14 is a longitudinal section view of the biopsy probe similar to FIG. 11, illustrating the simultaneous rotation and distal advancement of the cutter and the marked, severed tissue specimen contained within the cutter.

FIGS. 11 through 14 illustrate generally the steps necessary to harvest a tissue specimen utilizing the biopsy apparatus of the present invention. Referring to FIG. 11, needle 20 is advanced into lesion 68 with cutter 24 in its most distal position to close off bowl 34 to prevent snagging and tearing of tissue during linear movement of needle 20. Referring now to FIG. 12, after needle 20 has been positioned at the desired location in lesion 68 cutter 24 is retracted proximally. In FIG. 13, the vacuum source in control module 18 (see FIG. 1) is activated. Vacuum is communicated from control module 18 via flexible tubing to a fitting on lower lumen 32 in needle 20. As a result, a region of low pressure is created in lower lumen 32, which is in fluid communication via vacuum holes 36, with bowl 34 in upper lumen 30. Hence, the vacuum facilitates the prolapse of tissue against bowl bottom 38 in bowl 34. Once the tissue is fully prolapsed into bowl 34, marker element 26 is momentarily activated, leaving a mark 70 on the tissue, identifying the surface of the tissue that is in contact with bowl bottom 38. Referring to FIG. 14, motors in control module 18 communicate with gears in probe driver 22 via flexible cables to effect rotation and distal translation of cutter 24 through bowl 34, severing the tissue. Vacuum is then terminated and cutter 24 is retracted to the proximal end of needle 20 where the marked tissue specimen is retrieved by the clinician.

Figure 15:
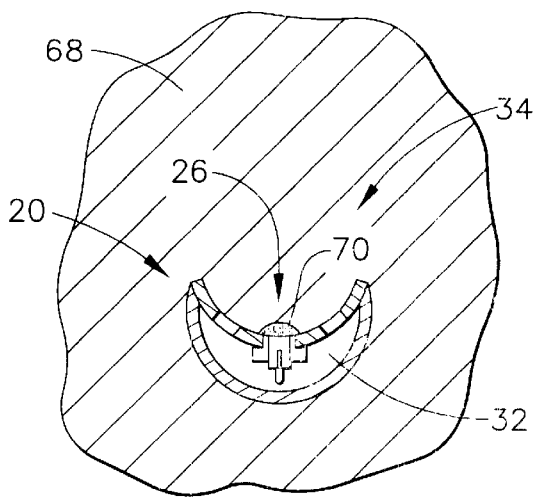
FIG. 15 is a cross sectional view taken along line 15—15 of FIG. 13.
Figure 17:
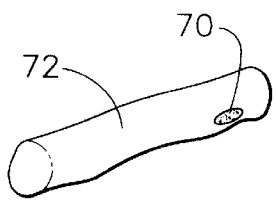
FIG. 17 is an isometric view of the first tissue specimen illustrating a mark on the perimeter of the specimen.
Figure 18:
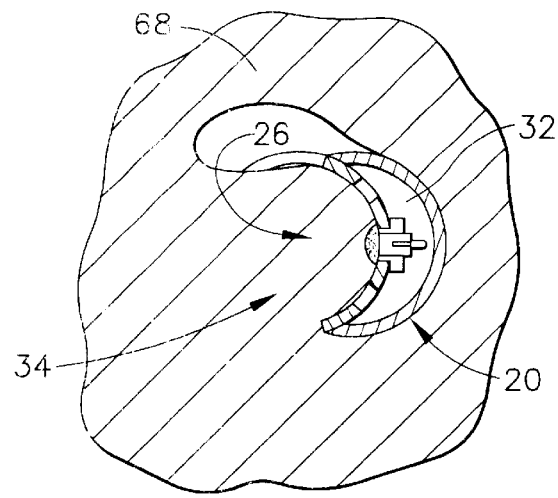
FIG. 18 is a cross sectional view similar to FIG. 15, illustrating that the biopsy probe has been rotated about its axis to take a second tissue sample.
Figure 16:
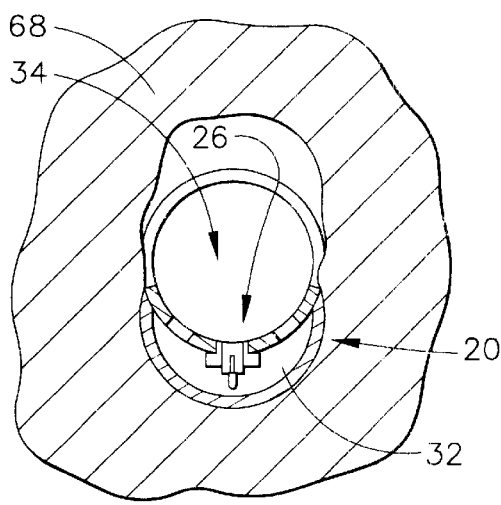
FIG. 16 is a cross sectional view similar to FIG. 15, illustrating a first tissue specimen having been cut, the cutter retracted, and the specimen removed.
Figure 19:
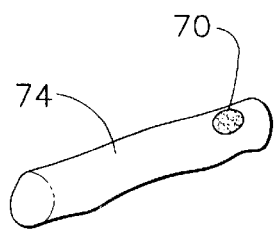
FIG. 19 is an isometric view of the second tissue specimen again illustrating a mark on the perimeter of the specimen.
Figure 20:
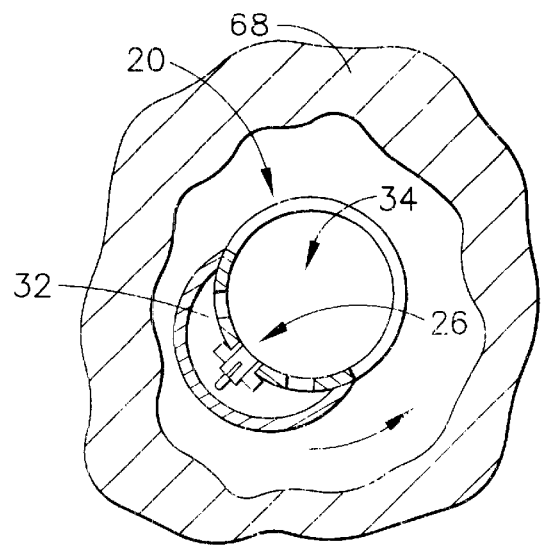
FIG. 20 is a cross sectional view similar to FIG. 15, illustrating the space remaining in the tissue mass after multiple tissue specimens have been harvested.

FIGS. 15 through 20 illustrate a procedure whereby multiple tissue specimens may be marked and acquired by rotating needle 20 to different angular positions. FIG. 15 is a cross sectional view taken along line 15—15 of FIG. 13, and shows needle 20 angularity positioned with bowl 34 in an upright or 12 o'clock position within lesion 68. Vacuum has been initiated through lower lumen 32 which effects the prolapse of tissue into bowl 34, pulling tissue into contact with marker element 26. Marker element 26 is momentarily activated, leaving a mark 70 on the surface of the tissue in contact with marker element 26. FIG. 16 is a cross sectional view similar to FIG. 15, whereas a first tissue specimen 72 has been cut, vacuum terminated, cutter 24 retracted, and first tissue specimen 72 removed. FIG. 17 illustrates first tissue specimen 72 with identifying mark 70 on the outer surface indicating the surface of the specimen that was in contact with marker element 26 in situ. FIG. 18 is a cross sectional view similar to FIG. 15, wherein the clinician has elected to rotate needle 20 approximately 90 degrees to the 9 o'clock position. Again, vacuum is applied, marker element 26 is momentarily activated, and second tissue specimen 74 is cut. FIG. 19 illustrates second tissue specimen 74 with identifying mark 70 on the outer surface indicating the surface of the specimen that was in contact with marker element 26 in situ. The clinician would continue to rotate needle 20 to different angular positions and repeat this process until the desired number of tissue specimens is taken. FIG. 20 is a cross sectional view similar to FIG. 15 illustrating the cavity remaining in lesion 68 after multiple tissue specimens have been removed.

Figure 21:
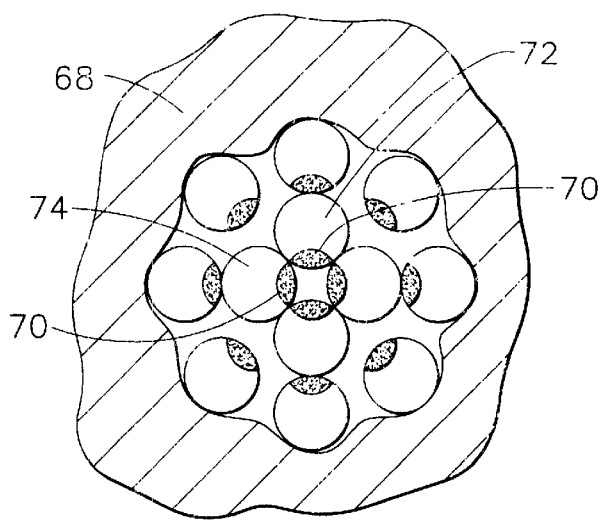
FIG. 21 illustrates the reconstruction of the harvested tissue mass from the multiple specimens, and illustrates using the mark on each specimen to determine correct radial orientation of each specimen.

FIG. 21 illustrates the reconstruction of the tissue mass removed in multiple pieces, showing a mark on each tissue specimen used to identify the proper radial orientation of the specimen as it was in situ. Lesion 68 is shown to illustrate the relationship of each specimen to the cavity resulting from the removal of multiple specimens. First tissue specimen 72 is shown at the 12 o'clock position with identifying mark 70 properly oriented to the center of lesion 68. Second tissue specimen 74 is shown at the 9 o'clock position with identifying mark 70 properly oriented again to the center of lesion 68. Subsequent tissue specimens are illustrated to show their orientations relative to lesion 68.

It should be noted that if multiple marker elements 26 are employed in the construction of needle 20 as discussed previously, multiple identifying marks 70 may be evident in FIGS. 17 and 19, provding to the clinician not only radial orientation information on each specimen but also information on the sequence in which each specimen was removed.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A biopsy probe for collection of at least one soft tissue sample from a surgical patient, said biopsy probe comprising:
   a) a handle having a distal end and a proximal end;
   b) an elongated needle, located at said distal end of said handle, said needle having a sharpened distal end for piercing tissue and a bowl proximal thereto for receiving a tissue mass;
   c) a cutter for severing a tissue mass received in said bowl; and
   d) at least one tissue marker element associated with a surface of said bowl, said tissue marker element adapted to apply a mark to an exterior of a tissue mass received in said bowl.

2. The biopsy probe of claim 1 wherein said at least one tissue marker element is disposed within a distal end of said bowl.

3. The biopsy probe of claim 1 wherein said at least one tissue marker element is disposed within a proximal end of said bowl.

4. The biopsy probe of claim 1 wherein said at least one tissue marker element comprises a RF element for marking tissue.

5. The biopsy probe of claim 1 wherein said at least one tissue marker element comprises a heating element for marking tissue.

6. The biopsy probe of claim 1 wherein said at least one issue marker element comprises a dye applicator for marking tissue.

7. The biopsy probe of claim 1 further including multiple tissue marker elements.

8. A biopsy probe for collection of at least one soft tissue sample from a surgical patient, said biopsy probe comprising:
   a) a driver portion having a distal end and a proximal end;
   b) an elongated needle at said distal end of said driver portion, said needle having a sharpened distal end for piercing tissue, and a bowl proximal thereto for receiving a tissue mass, said needle further including upper and lower lumens extending longitudinally therethrough, said lower lumen in fluid communication with a bottom of said bowl;
   c) a vacuum source for applying a vacuum through said lower lumen to facilitate prolapse of a tissue mass into said bowl;
   d) a cutter disposed coaxially on a longitudinal axis of said upper lumen, said cutter being moveable relative to said upper lumen for severing a tissue mass received in said bowl;
   e) at least one tissue marker element associated with a surface of said bowl, said tissue marker element adapted to apply a mark to an exterior of a tissue mass within said bowl.

9. The biopsy probe of claim 8 wherein said at least one tissue marker element is located at a distal end of said bowl.

10. The biopsy probe of claim 8 wherein said at least one tissue marker element is located at a proximal end of said bowl.

11. The biopsy probe of claim 8 wherein said at least one tissue marker element comprises a RF element for marking tissue.

12. The biopsy probe of claim 8 wherein said at least one tissue marker element comprises a heating element for marking tissue.

13. The biopsy probe of claim 8 wherein said at least one tissue marker element comprises a dye applicator for marking tissue.

14. The biopsy probe of claim 8 further including multiple tissue marker elements.

15. The biopsy probe of claim 8 wherein said at least one tissue marker element is disposed within an aperture at said bottom of said bowl, said marker element comprising:
   a) a marker rod and an insulator ring surrounding said marker rod;
   b) a first conductor wire connecting said marker rod to an RF energy source;

c) a second conductor wire connecting said needle to said RF energy source.

16. The biopsy probe of claim 8 wherein said at least one tissue marker element is disposed within an aperture at said bottom of said bowl, said marker element comprising:
   a) a marker rod and an insulator ring surrounding said marker rod;
   b) a first conductor wire connecting said marker rod to an RF energy source; and
   c) a second conductor wire adapted to be connected between a surgical patient and said RF energy source.

17. The biopsy probe of claim 8 wherein said at least one tissue marker element is disposed within an aperture at said bottom of said bowl, said marker element comprising: a heater housing;
   a) a heater fixed to said heater housing;
   b) an insulator ring surrounding said heater housing; and
   c) at least one conductor wire connected between said heater and an electric current source.

18. The biopsy probe of claim 8 wherein said at least one tissue marker element is disposed within an aperture at said bottom of said bowl, said marker element comprising:
   a) a flange connected to said aperture;
   b) a tube connected between said flange and a dye reservoir;
   c) means for injecting dye from said reservoir, through said tube and onto a tissue sample.

19. A method of using a biopsy probe to take a tissue specimen percutaneously and applying a mark in situ to said tissue specimen comprising the steps of:
   a) gathering a tissue specimen with a tissue receiving bowl;
   b) marking the radial position of the tissue specimen within said tissue receiving bowl by marking the tissue specimen on an exterior thereof; and
   c) severing and retrieving the tissue specimen.

20. The method of claim 19 wherein marking the radial position of the tissue specimen by marking the tissue specimen on an exterior thereof is done by marking a distal end of said tissue specimen.

21. The method of claim 19 wherein marking the radial position of the tissue specimen by marking the tissue specimen on an exterior thereof is done by marking a proximal end of said tissue specimen.

22. The method of claim 19 further comprising the step of marking the radial position of the tissue specimen by marking the tissue specimen on an exterior thereof multiple times.

* * * * *